(12) United States Patent
Ellis et al.

(10) Patent No.: US 6,371,962 B1
(45) Date of Patent: *Apr. 16, 2002

(54) STENT DELIVERY SYSTEM WITH STENT SECUREMENT MEANS

(75) Inventors: Louis G. Ellis, St. Anthony; Andrew J. Dusbabek, Dayton; Christopher R. Larson, St. Paul; Terry V. Brown, Fridley, all of MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/420,249

(22) Filed: Oct. 19, 1999

Related U.S. Application Data

(63) Continuation of application No. 08/702,150, filed on Aug. 23, 1996, now Pat. No. 6,007,543.

(51) Int. Cl.⁷ .............................................. A61F 11/00
(52) U.S. Cl. .................................... 606/108; 606/194
(58) Field of Search ............................. 606/194, 195, 606/198, 108

(56) References Cited

U.S. PATENT DOCUMENTS

| | | | |
|---|---|---|---|
| 4,328,056 A | 5/1982 | Snooks | |
| 4,338,942 A | 7/1982 | Fogarty | |
| 4,423,725 A | 1/1984 | Baran et al. | |
| 4,608,984 A | 9/1986 | Fogarty | |
| 4,733,665 A | 3/1988 | Palmaz | |
| 4,740,207 A | 4/1988 | Kreamer | |
| 4,744,366 A | 5/1988 | Jang | |
| 4,848,343 A | 7/1989 | Walstein et al. | |
| 4,875,480 A | 10/1989 | Imbert | |
| 4,950,227 A | * 8/1990 | Savin et al. | 606/192 |
| 5,007,926 A | 4/1991 | Derbyshire | |
| 5,026,377 A | 6/1991 | Burton et al. | |
| 5,037,392 A | 8/1991 | Hillstead | |

(List continued on next page.)

FOREIGN PATENT DOCUMENTS

| | | |
|---|---|---|
| EP | 0 266 957 A2 | 5/1988 |
| EP | 0 442 657 A2 | 9/1991 |
| EP | 0 257 091 B1 | 7/1993 |
| EP | 0 553 960 A1 | 8/1993 |
| EP | 0 627 201 A1 | 12/1994 |
| EP | 0 699 451 A2 | 3/1996 |
| EP | 0 707 837 A1 | 4/1996 |
| WO | WO 93/19703 | 10/1993 |
| WO | WO 96/03072 | 2/1996 |
| WO | WO 96/03092 A1 | 2/1996 |

OTHER PUBLICATIONS

Julio C. Palmaz et al., Expandable Intraluminal Graft: A Preliminary Study, Work in Progress, From the Departments of Radioloty (J.C.P., R.R.S., S.R.R.) and Pathology (F.O.T.) Universtiy of Texax Health Science Center at Sanantonio and Memorial Medical Center (W.J.K.), Corpus Christi, Texas, *Radiology*, vol. 356, No. 1, pp. 73–77.

*Primary Examiner*—Justine R. Yu
(74) *Attorney, Agent, or Firm*—Vidas, Arrett & Steinkraus

(57) ABSTRACT

A stent delivery system to facilitate introduction and placement of a stent, including a catheter having an expandable distal portion constructed and arranged for expanding the outer diameter of the catheter from a contracted state to an expanded state: a stent positioned around the distal portion of the catheter having a contracted condition and being expandable to an expanded condition, and being sized in the contracted condition to closely surround the catheter in the contracted state, the expandable distal portion of the catheter including a balloon within which there is included on the catheter shaft at least one body of a diameter larger than the catheter shaft to which the stent and balloon are fitted, as by crimping, for holding the stent in place until it is released therefrom by expansion of the balloon.

37 Claims, 4 Drawing Sheets

U.S. PATENT DOCUMENTS

| | | |
|---|---|---|
| 5,049,132 A | 9/1991 | Shaffer et al. |
| 5,108,416 A * | 4/1992 | Ryan et al. .................. 606/194 |
| 5,116,318 A | 5/1992 | Hillstead |
| 5,158,548 A | 10/1992 | Lau et al. |
| 5,226,880 A | 7/1993 | Martin |
| 5,226,889 A | 7/1993 | Sheiban |
| 5,242,399 A | 9/1993 | Lau et al. |
| 4,733,665 C1 | 1/1994 | Palmaz |
| 5,290,306 A | 3/1994 | Trotta et al. |
| 5,304,198 A * | 4/1994 | Samson ...................... 606/194 |
| 5,342,305 A | 8/1994 | Shonk |
| 5,344,402 A | 9/1994 | Crocker |
| 5,344,426 A | 9/1994 | Lau et al. |
| 5,358,487 A | 10/1994 | Miller |
| 5,364,354 A * | 11/1994 | Walker et al. ................. 604/96 |
| 5,378,237 A | 1/1995 | Boussignac et al. |
| 5,403,341 A | 4/1995 | Solar |
| 5,405,380 A | 4/1995 | Gianotti et al. |
| 5,409,495 A * | 4/1995 | Osborn ...................... 606/108 |
| 5,415,664 A | 5/1995 | Pinchuk |
| 5,441,515 A * | 8/1995 | Khosravi et al. ........... 606/194 |
| 5,445,646 A * | 8/1995 | Euteneuer et al. .......... 606/198 |
| 5,447,497 A | 9/1995 | Sogard et al. |
| 5,453,090 A | 9/1995 | Martinez et al. |
| 5,458,615 A | 10/1995 | Klemm et al. |
| 5,470,313 A | 11/1995 | Crocker et al. |
| 5,507,768 A | 4/1996 | Lau et al. |
| 5,512,051 A | 4/1996 | Wang et al. |
| 5,534,007 A | 7/1996 | St. Germain et al. |
| 5,536,252 A | 7/1996 | Imran et al. |
| 5,571,086 A * | 11/1996 | Kaplan et al. ................ 604/96 |
| 5,571,089 A * | 11/1996 | Crocker ...................... 604/96 |
| 5,591,228 A * | 1/1997 | Edoga ........................ 606/194 |
| 5,632,760 A * | 5/1997 | Sheiban et al. ............. 606/195 |
| 5,653,691 A * | 8/1997 | Rupp et al. ................... 604/96 |
| 5,817,102 A | 10/1998 | Johnson et al. ............. 606/108 |
| 5,846,246 A * | 12/1998 | Dirks et al. ................. 606/108 |

* cited by examiner

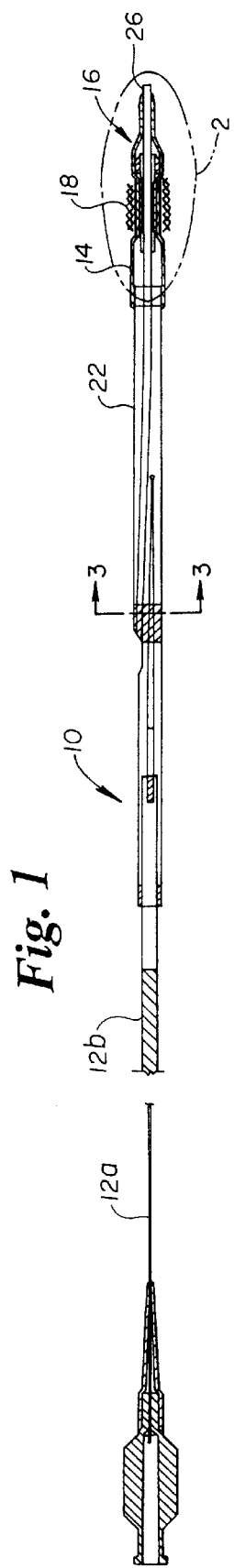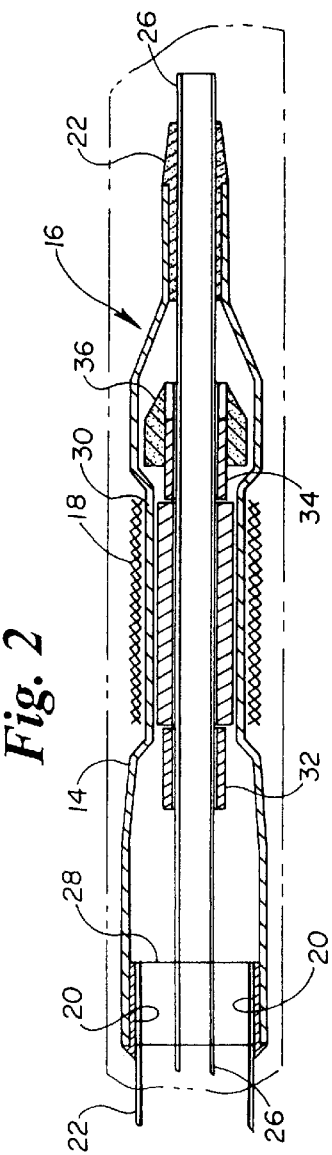

STENT DELIVERY SYSTEM WITH STENT SECUREMENT MEANS

RELATED APPLICATIONS

The present application is a continuation of U.S. application Ser. No. 08/702,150, filed on Aug. 23, 1996, now U.S. Pat. No. 6,007,543, which is incorporated herein by reference in its entirety.

BACKGROUND OF THE INVENTION

In typical PTCA procedures, a guiding catheter is percutaneously introduced into the cardiovascular system of a patient through a vessel and advanced through therein until the distal end thereof is at a desired location in the vasculature. A guidewire and a dilatation catheter having a balloon on the distal end thereof are introduced through the guiding catheter with the guidewire sliding through the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, the flexible, expandable, preformed balloon is inflated to a predetermined size with a liquid or gas at relatively high pressures, such as greater than about four atmospheres, to radially compress the arthrosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To prevent restenosis and strengthen the area, a physician can implant an intravascular prosthesis for maintaining vascular patency, called a stent, inside the artery at the lesion. The stent is expanded to a larger diameter for placement in the vasculature, often by the balloon portion of the catheter. Stents delivered to a restricted coronary artery, expanded to a larger diameter as by a balloon catheter, and left in place in the artery at the site of a dilated lesion are shown in U.S. Pat. No. 4,740,207 to Kreamer; U.S. Pat. No. 5,007,926 to Derbyshire; U.S. Pat. No. 4,733,665 to Palmaz; U.S. Pat. No. 5,026,377 to Burton et al.; U.S. Pat. No. 5,158,548 to Lau et al.; U.S. Pat. No. 5,242,399 to Lau et al.; U.S. Pat. No. 5,344,426 to Lau et al.; U.S. Pat. No. 5,415,664 to Pinchuk; U.S. Pat. No. 5,453,090 to Martinez et al.; U.S. Pat. No. 4,950,227 to Savin; U.S. Pat. No. 5,403,341 to Solar; U.S. Pat. No. 5,108,416 to Ryan et al. and European Patent Application No. 707 837 A1 to Sheiban, all of which are incorporated herein by reference. A stent particularly preferred for use with this invention is described in PCT Application No. 960 3092 A1, published Feb. 8, 1996, the content of which is also incorporated herein by reference.

The present invention is particularly directed to improved arrangements for releasably attaching the stent to the catheter to facilitate delivery thereof.

SUMMARY OF THE INVENTION

This invention concerns apparatus suitable for delivery of stents to body cavities. In general, stents are prosthetic devices which can be positioned within a body cavity, for example, a blood vessel of the body of a living human or in some other difficultly accessible place. The stent prosthesis is formed of a generally tubular body, the diameter of which can be decreased or increased. Stents are particularly useful for permanently widening a vessel which is either in a narrowed state, or internally supporting a vessel damaged by an aneurysm. Such stents are typically introduced into the body cavity by use of a catheter. The catheter is usually of the balloon catheter type in which the balloon is utilized to expand the stent, which is positioned over the balloon, to place it in a selected location in the body cavity. The present invention is particularly directed to improved arrangements for releasably attaching the stent to the catheter to facilitate delivery thereof. The stent is held in place on the catheter by means of an enlarged body carried by the catheter shaft within the balloon to which the stent and balloon are fitted, as by crimping.

BRIEF DESCRIPTION OF THE FIGURES

FIG. 1 is an isometric view, a portion of which is enlarged and in longitudinal section, of a balloon catheter having a stent fixed to the catheter by being crimped thereto over the balloon;

FIG. 2 is an even more enlarged view in longitudinal cross-section of the distal end portion of the catheter of FIG. 1;

DESCRIPTION OF THE PREFERRED EMBODIMENTS

Figure 3:
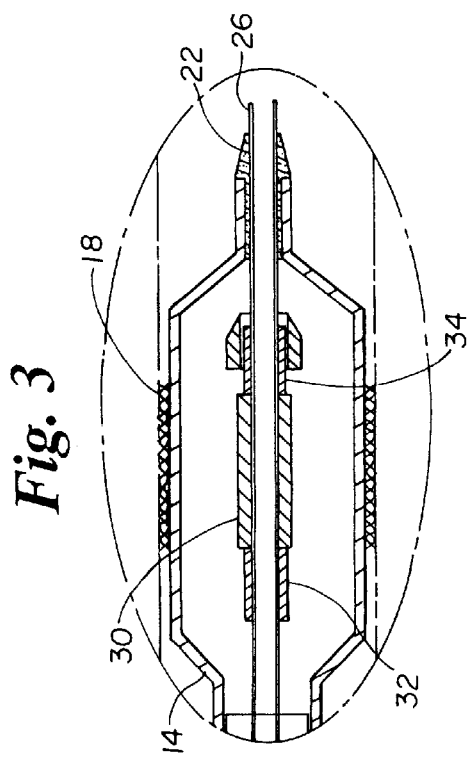
FIG. 3 is an enlarged cross-sectional view of the distal end portion of the catheter of FIG. 1 similar to that of enlarged view FIG. 2 but showing the balloon in an expanded condition along with the expanded stent.

Referring to FIGS. 1–3 a stent delivery system generally indicated at 10 includes a balloon catheter 12 having a balloon 14 on a distal end portion generally indicated at 16. FIG. 1 shows a proximal portion of the catheter at 12a and a distal portion 12b in enlarged view. FIG. 2 shows the distal end portion 16 in an even more enlarged view. The illustrative catheter 12 is of the type known as a rapid exchange or single operator catheter. However, other types of catheters may be used, such as over the wire and fixed wire types. The balloon 14 is fixed to the catheter 12 by standard means. The balloon is shown in its contracted state in FIGS. 1 and 2. A stent 18 is fixed about the balloon by crimping it thereto. The stent has a larger expanded diameter which is obtained when the balloon is expanded in the known manner. That is, the stent is released from the catheter upon expansion of the balloon as shown in FIG. 3 to be placed in a vessel. When the balloon is then deflated, removal of the balloon and catheter may be accomplished while leaving the stent in place.

As is known in the art the balloon is either bonded at its ends by adhesive 20 and 24, respectively to the outer member 22 of the catheter and to the inner member 26 of the catheter in the manner as shown, or is made one-piece with the outer member as is known in the art. The catheter balloon may be inflated by fluid (gas or liquid) from an inflation port extending from a lumen 28 contained in the catheter shaft and opening into the balloon as shown, or by other known arrangements, depending on the design of the catheter. The details and mechanics of balloon inflation and specific overall catheter construction will vary according to the particular design involved in any given instance, and are known in the art per se. All variations are acceptable for use with this invention.

Any balloon expandable stent may be used with this invention. Many are known in the art including plastic and metal stents. Some are more well known such as the stainless steel stent shown in U.S. Pat. No. 4,735,665; the wire stent shown in U.S. Pat. No. 4,950,227; another metal stent shown in European Patent Application EPO 707 837 A1 and that shown in U.S. Pat. No. 5,445,646. All of these patents are incorporated herein by reference. Also, shape memory metal stents may be used. As already indicated the stent of PCT Application 960 3092 A1 is particularly preferred.

The stent is typically about 16mm long, while the balloon may be 20 mm long. These dimensions, however, are merely representative for illustrative purposes only and are not meant to be limiting. The stent is positioned over the balloon portion of the dilatation catheter and gently crimped onto the balloon either by hand or with a tool such as a pliers or the like to be mounted for delivery as shown in FIGS. 1 and 2. The crimping may be accomplished by either the manufacturer or the physician.

In accordance with this invention, a mounting body 30, best seen in FIGS. 2 and 3, is included inside balloon 14 to provide a cushion and/or substrate of enlarged diameter relative to the stent shaft to support and hold the stent and secure it during crimping and the delivery procedure. The mounting body may be located only in the body portion of the balloon or may extend into either or both of the cone portions of the balloon.

In the embodiment shown, mounting body 30 is cylindrical in form and takes the shape of a sleeve carried on inner lumen 26, providing an enlarged area or portion for receiving the balloon and stent when the latter is crimped. Marker bands 32 and 34 may also be included on inner 26 as shown. Any radiopaque material such as gold is useful for this purpose. A stop member 36 of generally conical shape or any other shape may also be included on the distal marker band 34 as shown to provide additional resistance to stent movement during delivery and to protect the leading edge of the stent during delivery. A proximal stop member similar to member 36 (not shown) may be optionally included on marker band 32 if desired. Polyethylene or the like is suitable for the stop member(s). Although, the material of the mounting body may be hard, it is preferably of any deformable thermoplastic material, preferably an elastomer material and more preferably of a relatively resilient elastomer material, e.g., lower durometer silicone. A preferred deformable thermoplastic material is high density polyethylene (HDPE). A preferred lower durometer silicone is in the form of tubing. The deformation of resilient material of the mounting body when the stent/balloon is crimped to it causes a radial outward force on the stent/balloon increasing the friction therebetween despite a recoil of the stent.

During delivery, the balloon catheter is advanced through and positioned in a patient's vasculature so that the stent is adjacent to the portion of the vessel where treatment is to take place. The balloon is inflated to expand the stent to an enlarged diameter. When the stent has reached the desired diameter, the balloon is deflated so that the catheter may be removed leaving the stent in place.

Figure 4:
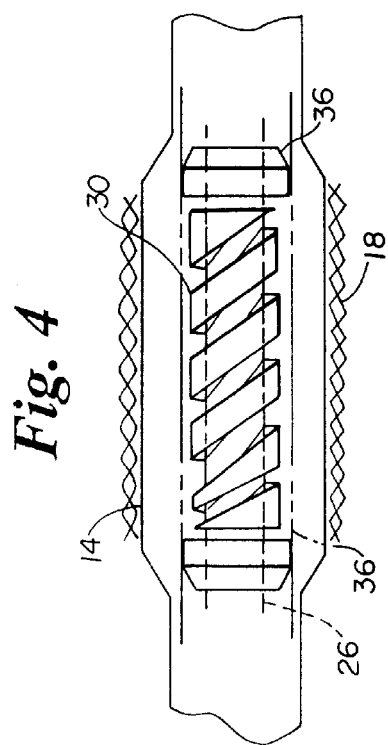
FIG. 4 is a schematic showing of a preferred mounting body carried by the catheter shaft within the balloon, the body being spirally cut to improve flexibility.

Another embodiment of the invention is shown in FIG. 4. In this embodiment the mounting body 30 is a spiral cut elastomer or other suitable material, such as a rigid or flexible plastic, to provide separation for flexibility in that portion of the catheter, allowing more easy movement or tracking around bends. The spiral cut may be only partly through the mounting body or may be all the way through as shown in FIG. 4. Also, while stop members 36 are shown at both ends of mounting body 30 in this embodiment, one, or no stop members may be used.

Figure 5:
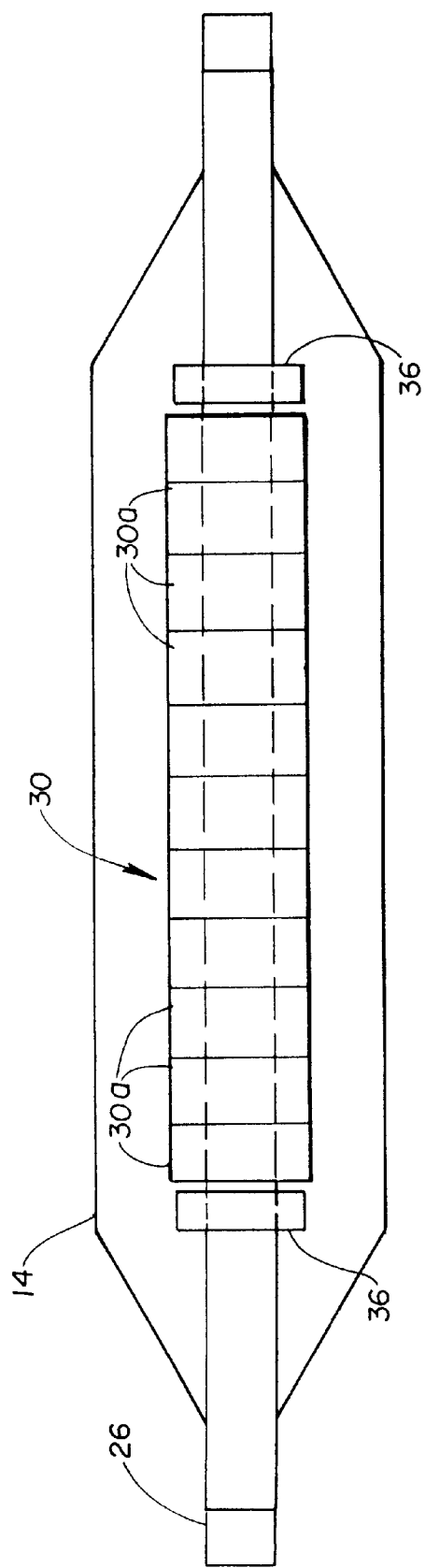
FIG. 5 is a schematic showing in cross-section of another embodiment of the invention with a stent not yet mounted.

Another similar version is shown in FIG. 5 which includes a cylindrical mounting body 30 made up of a plurality of separate adjacent rings 30a. Rings 30a may be individual bodies carried on the sheath or bodies cut from a cylinder partially separating them or fully separating them.

Figure 6:
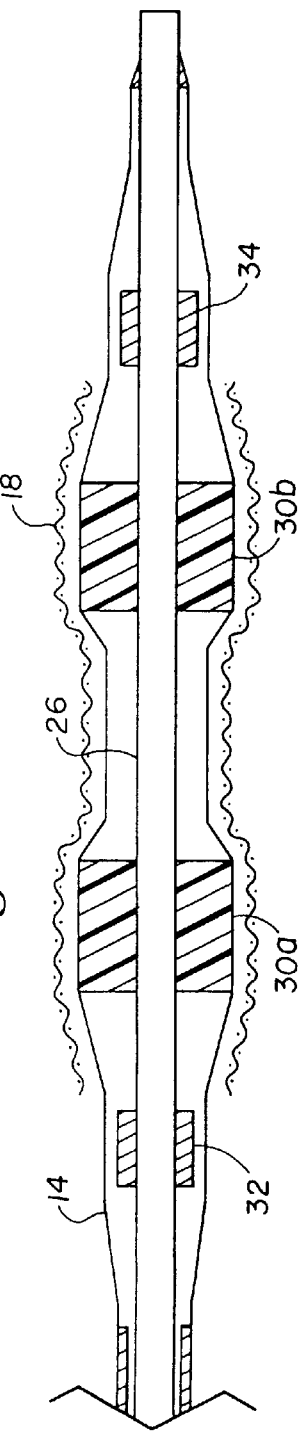
FIG. 6 is a schematic showing of another embodiment of the invention.

The embodiment shown in FIG. 6 includes another feature based on the geometry of the mounting body for further securing the stent upon crimping. This feature is referred to herein as interlocking. That is, the stent may be interlocked to the mount so that the stent cannot slide proximally or distally on the balloon unless it is deformed, such as by expansion. This can be seen by perusing the structure shown in FIG. 6 which includes the inner 26 having a two-piece mounting body made up of spaced mounting bodies 30a and 30b. The spacing between bodies 30a and 30b allows portions of the stent 18 and balloon 14 to be depressed or inserted between the bodies upon crimping of the stent thus forming an interlock against sliding longitudinally before the stent is released.

Figure 7:
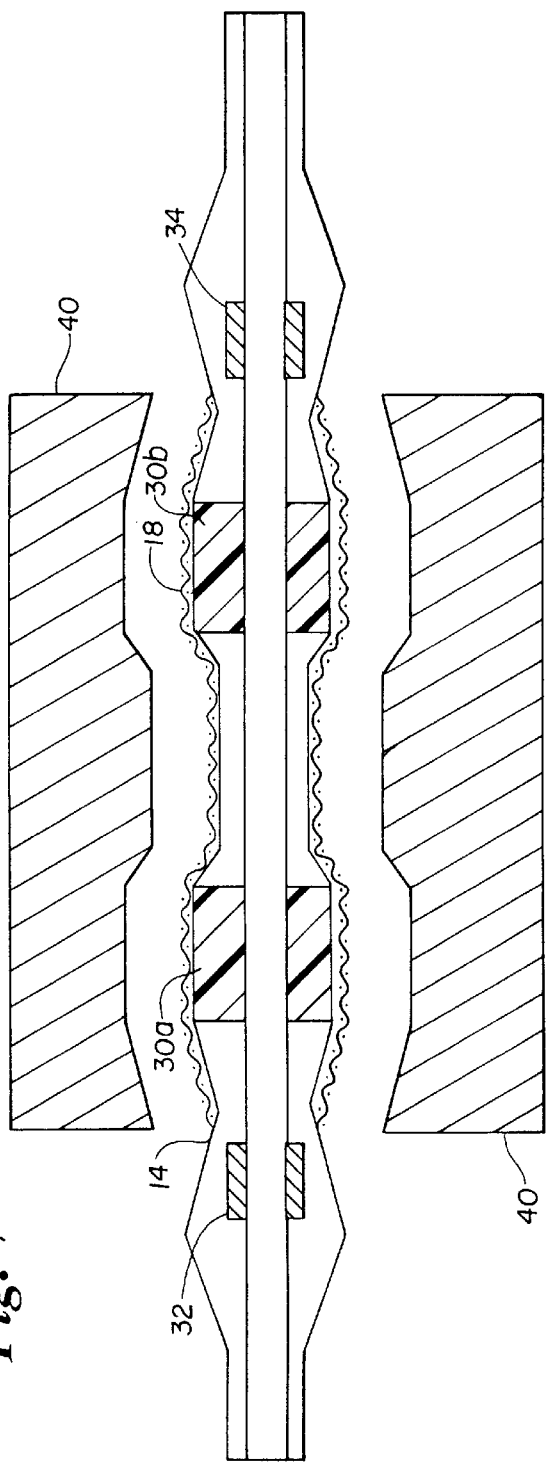
FIG. 7 is a schematic showing of a means for conveniently crimping the stent on the embodiment shown in FIG. 5.

The interlock formation or crimping is readily accomplished by a two-piece die 40 as shown in FIG. 7 or the like.

Figure 8:
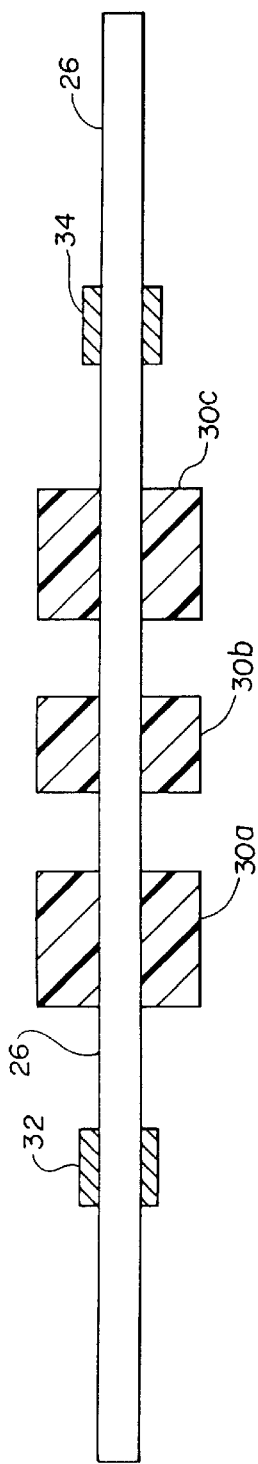
FIG. 8 is a schematic showing of yet another embodiment of the invention.

FIG. 8 demonstrates that more than a two-piece mounting body arrangement may be used if desired. In this embodiment, the mounting body is comprised of three spaced bodies 30a, 30b and 30c on the inner 26. Preferably in the embodiments of FIGS. 6 and 8, the mounting bodies will be ring-like in shape or cylindrical in shape although other configurations will be readily apparent to those familiar with this art.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent delivery system for carrying and delivering a stent having a first end and a second end and a contracted state and an expanded state, the system comprising:

a catheter having a shaft having a diameter and expandable inflatable means associated therewith at a distal part of the shaft and including mounting and retaining means for receiving the stent on the expandable inflatable means whereby the stent is radially expanded upon inflation of the inflatable means, the mounting and retaining means including at least one mounting body, the at least one mounting body having a length and an outer surface diameter and being carried on and surrounding the shaft inside the inflatable means whereby the diameter of the shaft is increased at the distal part for facilitating the mounting and retaining of the stent and wherein, when the stent is mounted on the catheter, the at least one mounting body is between the stent and the shaft, the outer surface diameter of the at least one mounting body being substantially constant along its length.

2. The stent delivery system of claim 1 wherein the mounting body is of a material which resiliently deforms under radial pressure.

3. The stent delivery system of claim 2 wherein the material is elastomeric.

4. The stent delivery system of claim 2 wherein the material comprises high density polyethylene.

5. The stent delivery system of claim 2 wherein the material comprises silicone.

6. The stent delivery system of claim 1 wherein the at least one mounting body includes at least one separation whereby the flexibility of the body and catheter is increased.

7. The stent delivery system of claim 6 wherein the separation is in the form of a spiral.

8. The stent delivery system of claim 1 wherein the stent is crimped to the mounting and retaining means for delivery.

9. The stent delivery system of claim 1, wherein the stent has two opposite ends, the stent delivery system further including a pair of stops, each of which is respectively positioned at the opposite ends of the stent and carried by the shaft inside the inflatable means.

10. The stent delivery system of claim 9 wherein the stops are conical in shape.

11. The stent delivery system of claim 1 further including marker bands positioned proximally and distally of the stent.

12. The stent delivery system of claim 1 wherein the inflatable means comprises a balloon.

13. The stent delivery system of claim 1 further including a stop carried by the shaft and positioned inside the inflatable means.

14. A stent delivery system comprising:
a catheter having a shaft and expandable inflatable means associated therewith at a distal part of the shaft and including mounting and retaining means for receiving a stent, the stent having a first end and a second end and a contracted state and an expanded state, to be delivered upon expansion of the inflatable means, the mounting and retaining means including at least one mounting body, the at least one mounting body being inside the inflatable means and carried on the shaft, the at least one mounting body being positioned on the shaft such that, when the stent is loaded onto the inflatable means and the shaft in the stent's contracted state, at least a portion of the at least one mounting body is under the stent, the at least one mounting body having a length and an outer surface diameter, wherein the outer surface diameter is substantially constant along the length, and
the stent crimped to the inflatable means and the at least one mounting body such that a portion of the stent is deformed to a diameter less than that of the at least one mounting body, thereby facilitating mounting and retaining of the stent.

15. The stent delivery system of claim 14 wherein the stent is generally tubular in shape and the at least one mounting body is uniformly cylindrical in shape.

16. The stent delivery system of claim 14 wherein at least two longitudinally spaced mounting bodies are included positioned between the stent and the shaft and a portion of the stent between the mounting bodies is additionally crimped to a lesser diameter than that of the mounting bodies and positioned between the mounting bodies.

17. The stent delivery system of claim 16 wherein the stent is generally tubular in shape and the mounting bodies are ring-shaped.

18. The stent delivery system of claim 14 wherein three longitudinally spaced mounting bodies are included between the stent and the shaft and the stent is crimped to a lesser diameter between the bodies.

19. The stent delivery system of claim 18 wherein the stent is generally tubular in shape and the mounting bodies are ring-shaped.

20. A balloon catheter for intraluminal delivery of a stent, the catheter comprising a shaft having a diameter, a balloon associated with a distal portion of the shaft for receiving a stent, the stent having a first end and a second end and a contracted state and an expanded state, and means for inflating the balloon, the shaft including at least one mounting body radially carried on the shaft inside the balloon, whereby the diameter of the shaft is increased inside the balloon to facilitate mounting and retaining of a stent to the catheter over the balloon, the at least one mounting body being positioned on the shaft such that when the stent is loaded onto the inflatable means and the shaft in the stent's contracted state at least a portion of the at least one mounting body is under the stent and between the first and second ends of the stent, the at least one mounting body having a length and an outer surface diameter, wherein the outer surface diameter is substantially constant along the length.

21. The catheter of claim 20 wherein the mounting body is of a material which resiliently deforms under radial pressure.

22. The catheter of claim 21 wherein the material is elastomeric.

23. The catheter of claim 21 wherein the material is high density polyethylene.

24. The catheter of claim 21 wherein the material is silicone.

25. The catheter of claim 20 wherein the mounting body comprises at least one separation whereby trackability of the catheter is improved.

26. The catheter of claim 25 wherein the separation is in a spiral configuration.

27. The catheter of claim 20 further including a pair of spaced stops.

28. The catheter of claim 27 wherein the stops are conical in shape.

29. The catheter of claim 20 further including spaced marker bands.

30. The catheter of claim 20 wherein the mounting body is uniformly cylindrical in shape.

31. The catheter of claim 20 wherein at least two longitudinally spaced mounting bodies are included, wherein the at least two mounting bodies are positioned between the stent and the shaft.

32. The catheter of claim 31 wherein the mounting bodies are ring-shaped.

33. The catheter of claim 20 wherein at least three longitudinally spaced mounting bodies are included positioned between the stent and the shaft.

34. The catheter of claim 33 wherein the mounting bodies are ring-shaped.

35. A stent delivery system comprising:
a radially expandable stent of generally cylindrical configuration, having a length, a first end and a second end and a contracted state and an expanded state, and a catheter having a shaft having a diameter and expandable inflatable means associated therewith at a distal part of the shaft, wherein the inflatable means comprises a balloon, and including mounting and retaining means for receiving the stent on the expandable inflatable means for radial expansion of the stent upon inflation of the inflatable means, the mounting retaining means including at least one mounting body carried on and surrounding the shaft inside the inflatable means, the at least one mounting body being at least ⅔ the length of the stent and being positioned on the shaft such that when the stent is loaded onto the inflatable means and the shaft in the stent's contracted state at least a portion of the at least one mounting body is under the stent and between the first and second ends of the stent, whereby the diameter of the shaft and inflatable portion are increased at the distal part for facilitating the mounting and retaining of the stent.

36. The stent delivery system of claim 35, the at least one mounting body comprising no more than one layer of material.

37. The stent delivery system of claim 36, wherein the material comprises high density polyethylene.

* * * * *